US008471010B2

(12) United States Patent
Frutos et al.

(10) Patent No.: US 8,471,010 B2
(45) Date of Patent: Jun. 25, 2013

(54) SYNTHESIS OF DIHYDROTHIENO[3,2-D]PYRIMIDINE DIOLS

(75) Inventors: Rogelio P. Frutos, Sandy Hook, CT (US); Thomas G. Tampone, Southbury, CT (US); Jason Alan Mulder, New Milford, CT (US); Dhileepkumar Krishnamurthy, Brookfield, CT (US); Chris H. Senanayake, Brookfield, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 250 days.

(21) Appl. No.: 12/989,575

(22) PCT Filed: May 7, 2009

(86) PCT No.: PCT/US2009/043068
§ 371 (c)(1),
(2), (4) Date: Jan. 11, 2011

(87) PCT Pub. No.: WO2009/140127
PCT Pub. Date: Nov. 19, 2009

(65) Prior Publication Data
US 2011/0130563 A1    Jun. 2, 2011

Related U.S. Application Data

(60) Provisional application No. 61/052,816, filed on May 13, 2008.

(51) Int. Cl.
*C07D 495/04*    (2006.01)
(52) U.S. Cl.
USPC .......................................... 544/278; 544/253

(58) Field of Classification Search
USPC ........................................................ 544/278
See application file for complete search history.

(56) References Cited

U.S. PATENT DOCUMENTS 3,318,881 A    5/1967    Ohnacker et al.
3,658,819 A    4/1972    Bertin et al.

FOREIGN PATENT DOCUMENTS
EP    1 544 202 A1    6/2005

OTHER PUBLICATIONS

Sekiya et al. (Eur. J. Med. Chem., 1980, 15(4), pp. 317-322).*
International Search Report for PCT/US2009/043068 mailed Dec. 14, 2009.
Szakonyi, Zsolt, et al; tert-Butylcyclopentane Derivates. Part 8. Synthesis of tert-Butylcyclopentane-fused Pyrimidin-4-Ones: Heterocycles (1996) vol. 42, No. 2 pp. 625-634.
Takaya, Takao, et al; Covenient Synthesis of 1,2-Ureylenecyclopentane Derivatives; Bulletin of the Chemical Society of Japan (1967) vol. 40, No. 12 pp. 2844-2849.

* cited by examiner

*Primary Examiner* — Susanna Moore
(74) *Attorney, Agent, or Firm* — Michael P. Morris; Timothy X. Witkowski

(57) ABSTRACT

The present invention relates to an improved process for the preparation of dihydrothieno[3,2-d]pyrimidine diols, and similar pyrimidine diols, that is efficient, high-yielding, and does not require expensive and potentially unstable intermediates. The diols are used as intermediates in the synthesis of pyrimidine compounds which inhibit PDE4, and are thus useful in the treatment of respiratory or gastrointestinal diseases and complaints, peripheral or central nervous system diseases and disorders, inflammatory conditions, and cancers.

21 Claims, No Drawings

SYNTHESIS OF DIHYDROTHIENO[3,2-D]PYRIMIDINE DIOLS

CROSS-REFERENCE TO RELATED APPLICATIONS

This application is the national phase entry under 35 U.S.C. §371 of International Application No. PCT/US2009/043068, filed May 7, 2009, which claims priority to U.S. Ser. No. 61/052,816, filed May 13, 2008, each of which is hereby incorporated by reference in its entirety.

FIELD OF THE INVENTION

The present invention relates to an improved method for preparing dihydrothieno[3,2-d]pyrimidine diols, particularly a 6,7-dihydro-thieno[3,2-d]pyrimidine-2,4-diol, and similar pyrimidine diols. More particularly, the present invention sets forth a method for preparing pyrimidine diols in an efficient, high-yielding reaction that does not require expensive and potentially unstable intermediates. The pyrimidine diols are useful for a variety of purposes including intermediates in the synthesis of pharmaceuticals.

DESCRIPTION OF RELATED ART

Dihydrothienopyrimidines are commonly synthesized from dihydrothieno[3,2-d]pyrimidine diols, for example, as described in U.S. Patent Publication 2007/0259846 and WO 2006/111549. The synthesis of the dihydrothieno[3,2-d]pyrimidine diol intermediates has proved challenging to implement in an efficient reaction that does not require expensive and potentially unstable intermediates and also results in obtaining the desired product in high yield and purity. For example, U.S. Pat. No. 3,318,881 reports the condensation of a keto-dihydrothiophene-2-carboxylic acid methyl ester with s-ethylisothiourea to form 2-ethylsulfanyl-6-7-dihydrothieno[3,2-d]pyrimidin-4-ol, which can then be subjected to acid hydrolysis to yield a dihydrothieno[3,2-d]pyrimidine diol as described in U.S. Patent Publication No. 2007/0259846. This process, however, provides only modest yields, requires the use of s-ethylisothiourea or other s-alkylisothioureas, which are expensive and have limited availability, and produces an unpleasant stench associated with the release of ethanethiol during the acid hydrolysis. Attempts to substitute the less expensive urea for the s-alkylisothiourea in the condensation reaction have been unsuccessful because of poor yields, for example as reported by Ohno et al. (1986) Chem. Pharm Bull. 34:4150.

Other pyrimidines may be synthesized from pyrimidine-2,4-diols, such as 6,7-dihydro-5H-cyclopentapyrimidine-2,4-diol, in modest yields. For example, diols reported by Sekiya et al. (1980) Eur. J. Med. Chem. 15, 4: 317 were used to generate 2,4-diamino-5,6-polymethlenepyrimidine derivatives for use as hypoglycemic, antihypertensive and anorexigenic agents. However, because of the above-discussed limitations, a need in the art to prepare intermediate diols via improved and efficient synthetic methods remains.

BRIEF DESCRIPTION OF THE INVENTION

The present invention provides an improved, high-yield method for preparing dihydrothieno[3,2-d]pyrimidine diols, and similar pyrimidine-2,4-diols. The disclosed method for preparing a compound of formula I:

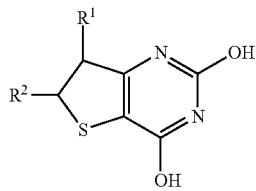

comprises reacting a starting compound of the formula II

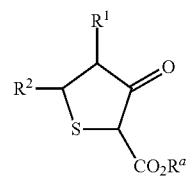

with urea, in the presence of acid, to yield an intermediate of the formula IV

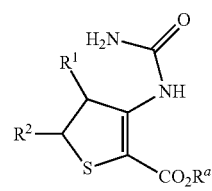

and cyclizing the intermediate of the formula IV with a base, to yield the final product of the formula I.

The present invention also provides a method for preparing additional pyrimidine diols. For example, a method for preparing a compound of formula X:

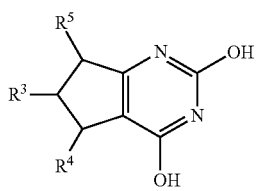

comprises reacting a starting compound of the formula VIII

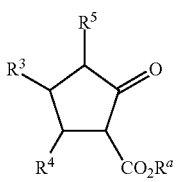

with urea, in the presence of acid, to yield an intermediate of the formula IX

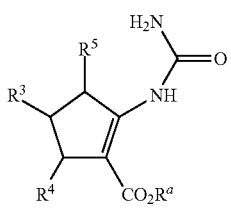

and cyclizing the intermediate of the formula IX with a base, to yield the final product of the formula X.

The acid may be selected from acetic acid, trifluoroacetic acid, perchloric acid, toluene sulfonic acid, hydrobromic acid, hydrochloric acid, sulfuric acid and nitric acid. In a preferred embodiment, the acid is hydrochloric acid. The base may be selected from the group consisting of metal hydride bases, metal alkoxide bases, and metal phosphate bases. In a preferred embodiment, the base is MeONa. In another preferred embodiment, the base is NaOH.

In one embodiment of the invention, the compound of formula I is 6,7-dihydro-thieno[3,2-d]pyrimidine-2,4-diol (formula Ia), 6-methyl-6,7-dihydro-thieno[3,2-d]pyrimidine-2,4-diol (formula Ib), 6-ethyl-6,7-dihydro-thieno[3,2-d]pyrimidine-2,4-diol (formula Ic), 6-phenyl-6,7-dihydro-thieno[3,2-d]pyrimidine-2,4-diol (formula Id), 6,6-dimethyl-6,7-dihydro-thieno[3,2-d]pyrimidine-2,4-diol (formula Ie) or 7-Methyl-6,7-dihydro-thieno[3,2-d]pyrimidine-2,4-diol (formula If).

In another embodiment of the invention, the compound of formula X is 9H-indeno[2,1-d]pyrimidine-2,4-diol (formula Xb).

The above and still further features and advantages of the present invention will become apparent upon consideration of the following detailed description of specific embodiments thereof.

DETAILED DESCRIPTION OF THE INVENTION

Reference will now be made in detail to the presently preferred embodiments of the invention, which, together with the following examples, serve to explain the principles of the invention. These embodiments are described in sufficient detail to enable those skilled in the art to practice the invention, and it is to be understood that other embodiments may be utilized, and that structural, physical, and chemical changes may be made without departing from the spirit and scope of the present invention. Unless otherwise defined, all technical and scientific terms used herein have the same meaning as commonly understood by one of ordinary skill in the art to which this invention belongs. Although any methods and materials similar or equivalent to those described herein can be used in the practice or testing of the present invention, the preferred methods, devices, and materials are now described.

The following abbreviations are used herein:
Bu=butyl;
HPLC=high-performance liquid chromatography;
iPr=isopropyl;
Me=methyl;
NMR=nuclear magnetic resonance;
LCMS (EI)=liquid chromatography mass spectrometry (electron impact)
t=tert; and
TLC=thin layer chromatography.

Terms not specifically defined herein should be given the meanings that would be given to them by one of skill in the art in light of the disclosure and the context. For example, "$C_{1-6}$ alkoxy" is a $C_{1-6}$ alkyl with a terminal oxygen, such as methoxy, ethoxy, propoxy, pentoxy and hexoxy. All alkyl, alkylene or alkynyl groups shall be understood as being branched or unbranched where structurally possible and unless otherwise specified.

Other more specific definitions are as follows:

The term "alkyl" refers to a saturated aliphatic radical containing from one to ten carbon atoms or a mono- or polyunsaturated aliphatic hydrocarbon radical containing from two to twelve carbon atoms unless otherwise stated. The mono- or polyunsaturated aliphatic hydrocarbon radical contains at least one double or triple bond, respectively. Examples of "alkyl" include alkyl groups that are straight chain alkyl groups containing from one to eight carbon atoms and branched alkyl groups containing from three to ten carbon atoms. Other examples include lower alkyl groups which are straight chain alkyl groups containing from one to six carbon atoms and branched alkyl groups containing from three to six carbon atoms. It should be understood that any combination term using an "alk" or "alkyl" prefix refers to analogs according to the above definition of "alkyl". For example, terms such as "alkoxy", "alkythio" refer to alkyl groups linked to a second group via an oxygen or sulfur atom. "Alkanoyl" refers to an alkyl group linked to a carbonyl group (C=O). Each alkyl or alkyl analog described herein shall be understood to be optionally partially or fully halogenated.

The term "cycloalkyl" refers to the cyclic analog of an alkyl group, as defined above. Examples of cycloalkyl groups are saturated or unsaturated nonaromatic cycloalkyl groups containing from three to eight carbon atoms, and other examples include cycloalkyl groups having three to six carbon atoms. Examples of "cycloalkyl" include, for example, cyclopropyl, cyclopentyl, and cyclohexyl.

The term "heterocycloalkyl" refers to a stable 4-8 membered (but preferably, 5 or 6 membered) monocyclic or 8-11 membered bicyclic heterocycle radical which may be either saturated or unsaturated, and is non-aromatic. Each heterocycle consists of carbon atoms and from 1 to 4 heteroatoms chosen from nitrogen, oxygen and sulfur. The heterocycle may be attached by any atom of the cycle, which results in the creation of a stable structure. Examples of "heterocycloalkyl" include radicals such as pyrrolinyl, pyrrolidinyl, pyrazolinyl, pyrazolidinyl, piperidinyl, morpholinyl, thiomorpholinyl, piperazinyl, indolinyl, azetidinyl, tetrahydropyranyl, tetrahydrothiopyranyl, tetrahydrofuranyl, hexahydropyrimidinyl, hexahydropyridazinyl, dihydro-oxazolyl, 1,2-thiazinanyl-1,1-dioxide, 1,2,6-thiadiazinanyl-1,1-dioxide, isothiazolidinyl-1,1-dioxide and imidazolidinyl-2,4-dione.

The term "halogen" refers to bromine, chlorine, fluorine or iodine. As used herein above and throughout this application, "nitrogen" and "sulfur" include any oxidized form of nitrogen and sulfur and the quaternized form of any basic nitrogen.

The term "aryl" shall be understood to mean a 6-12 membered aromatic carbocycle, which can be a single ring or can be multiple rings fused together or linked covalently. The term "aryl" includes, for example, phenyl and naphthyl; other terms comprising "aryl" will have the same definition for the aryl component, examples of these moieties include: arylalkyl, aryloxy or arylthio.

The term "heteroaryl" refers to a stable 5-8 membered (but preferably, 5 or 6 membered) monocyclic or 8-11 membered bicyclic aromatic heterocycle radical. Each heterocycle consists of carbon atoms and from 1 to 4 heteroatoms chosen from nitrogen, oxygen and sulfur. The heteroaryl group may be attached by any atom of the ring which results in the creation of a stable structure. Examples of "heteroaryl"

include radicals such as furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolizinyl, indolyl, isoindolyl, benzofuranyl, benzothienyl, indazolyl, benzimidazolyl, benzthiazolyl, benzoxazolyl, purinyl, quinolizinyl, quinolinyl, isoquinolinyl, cinnolinyl, phthalazinyl, quinazolinyl, quinoxalinyl, naphthyridinyl, pteridinyl, carbazolyl, acridinyl, phenazinyl, phenothiazinyl and phenoxazinyl.

The terms "optional" or "optionally" mean that the subsequently described event or circumstances may or may not occur, and that the description includes instances where the event or circumstance occurs and instances in which it does not. For example, "optionally substituted aryl" means that the aryl radical may or may not be substituted and that the description includes both substituted aryl radicals and aryl radicals having no substitution.

The term "substituted" means that any one or more hydrogens on an atom of a group or moiety, whether specifically designated or not, is replaced with a selection from the indicated group of substituents, provided that the atom's normal valency is not exceeded and that the substitution results in a stable compound. If a bond to a substituent is shown to cross the bond connecting two atoms in a ring, then such substituent may be bonded to any atom on the ring. When a substituent is listed without indicating the atom via which such substituent is bonded to the rest of the compound, then such substituent may be bonded via any atom in such substituent. For example, when the substituent is piperazinyl, piperidinyl, or tetrazolyl, unless specified otherwise, such piperazinyl, piperidinyl, or tetrazolyl group may be bonded to the rest of the compound of the invention via any atom in such piperazinyl, piperidinyl, or tetrazolyl group. Generally, when any substituent or group occurs more than one time in any constituent or compound, its definition on each occurrence is independent of its definition at every other occurrence. Thus, for example, if a group is shown to be substituted with 0 to 2 R, then such group is optionally substituted with up to two R groups and R at each occurrence is selected independently from the defined list of possible R. Such combinations of substituents and/or variables, however, are permissible only if such combinations result in stable compounds.

The present invention relates to a novel strategy for the synthesis of dihydrothieno[3,2-d]pyrimidine diols, and similar pyrimidine-2,4-diols, that provides for higher yields, more efficient reactions, and overcoming many of the prior art problems associated with the large-scale production of dihydrothieno[3,2-d]pyrimidine diols, and similar pyrimidin-2,4-diols. The strategy provides an efficient synthetic scheme that does not require expensive or potentially unstable intermediates, and can be carried out as a "one-pot" reaction if desired.

Methods for making the compounds of the formulas (I) and (X) are described herein. The compounds of the invention may be prepared by the general methods and examples presented below, and additional methods known to those of ordinary skill in the art. Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Examples section. Reaction progress may be monitored by conventional methods such as TLC or HPLC. Intermediates and products may be purified by methods known in the art, including column chromatography, HPLC or recrystallization.

The preferred methods provide processes of making a dihydrothieno[3,2-d]pyrimidine diol of formula I, e.g.,:

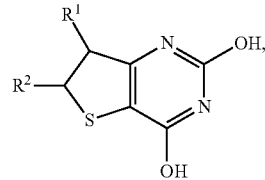

wherein $R^1$ and $R^2$ independently ndependently selected from H, alkyl, cycloalkyl, aryl, heteroaryl, heterocycloalkyl, halogen, alkoxy, aryloxy, cycloalkoxy, heteroaryloxy, heterocycloalkoxy, $-NO_2$, $-NRR'$, haloalkyl, haloalkoxy, $-SH$, $-S$-alkyl, $-SO_2$-alkyl, $-SO_2NH_2$, $-SO_2NH$-alkyl, and $-SO_2N(alkyl)_2$, preferably from H, alkyl, alkoxy, halogen, haloalkyl, haloalkoxy and $-NRR'$; and wherein R and R' are H or alkyl.

The preferred methods also provide processes of making 2,4-pyrimidine diols of formula X, e.g.,:

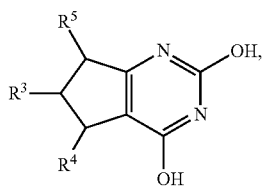

wherein $R^3$ and $R^4$ are independently selected from H, alkyl, cycloalkyl, aryl, heteroaryl, heterocycloalkyl, halogen, alkoxy, aryloxy, cycloalkoxy, heteroaryloxy, heterocycloalkoxy, $-NO_2$, $-NRR'$, haloalkyl, haloalkoxy, $-SH$, $-S$-alkyl, $-SO_2$-alkyl, $-SO_2NH_2$, $-SO_2NH$-alkyl, and $-SO_2N(alkyl)_2$, with the proviso that $R^3$, $R^4$ and $R^5$ cannot all be H; or $R^3$ and $R^4$ are combined with the carbon atoms to which they are attached to form a ring selected from the group consisting of benzene, pyridine, pyrimidine, pyrazine, cyclohexane, piperidine, piperazine, morpholine, thiomorpholine, a partially or fully hydrated pyrimidine and naphthalene, which optionally may be substituted by a residue selected from among alkyl, cycloalkyl, aryl, heteroaryl, heterocycloalkyl, halogen, alkoxy, aryloxy, cycloalkoxy, heteroaryloxy, heterocycloalkoxy, $-NO_2$, $-NRR'$, haloalkyl, haloalkoxy and hydroxy;

R5 is selected from H, alkyl, cycloalkyl, aryl, heteroaryl, heterocycloalkyl, halogen, alkoxy, aryloxy, cycloalkoxy, heteroaryloxy, heterocycloalkoxy, $-NO_2$, $-NRR'$, haloalkyl, haloalkoxy, $-SH$, $-S$-alkyl, $-SO_2$-alkyl, $-SO_2NH_2$, $-SO_2NH$-alkyl, and $-SO_2N(alkyl)_2$, preferably from H, alkyl, alkoxy, halogen, haloalkyl, haloalkoxy and $-NRR'$; and wherein R and R' are each independently selected from H or alkyl.

As illustrated in Scheme 1, an embodiment of the present invention, compounds of formula I may be prepared starting with an acid-catalyzed condensation between a 3-keto-dihydrothiophene-2-carboxylic acid alkyl ester of formula II, wherein $R^a$ is alkyl, and urea (III), to yield a 3-ureido-dihydrothiophene-2-carboxylic acid alkyl ester of formula IV. The compound of formula IV is then cyclized to yield a dihydrothieno[3,2-d]pyrimidine diol of formula I. The cyclization is preferably performed under basic conditions. The condensation and cyclization reactions may be carried out in separate steps, or may be combined in a "one-pot" procedure. The product, a compound of formula I, may be further modified by methods known in the art to produce additional compounds such as dihydrothieno[3,2-d]pyrimidines.

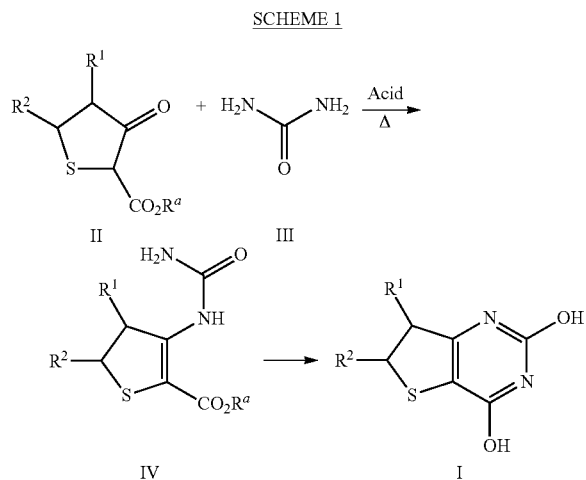

SCHEME 1

The condensation reaction of the compounds of formulas II and III takes place in the presence of an acid catalyst, for example, acetic acid, trifluoroacetic acid, perchloric acid, toluene sulfonic acid, hydrobromic acid, hydrochloric acid, sulfuric acid, or nitric acid. In a preferred embodiment, the acid is a hydrochloric acid. An alcohol or mixture of alcohols may be used as a solvent, for example, methanol, ethanol, isopropanol, n-propanol, butanol, etc., may be used. Methanol is the preferred alcoholic solvent. The reaction may be carried out at temperatures between 0° C. and the reflux temperature of the solvent, and generally requires a period of 0.5 to 24 hours for completion, preferably about 2-6 hours, and more preferably about 4-6 or about 3-5 hours. The reaction may be run at ambient pressure, or at reduced or elevated pressures.

The above-described reaction yields a 3-ureido-dihydrothiophene-2-carboxylic acid alkyl ester of formula IV, which may be isolated at this time or may be left in the reaction vessel for a "one-pot" procedure. Isolation may be advantageous when removal of impurities is desired before the cyclization process, but is not required.

Whether isolated or not, the compound of formula IV is cyclized, preferably in the presence of a base, in a suitable solvent such as water or an alcohol, for example, methanol, ethanol, isopropanol, n-propanol, butanol, etc. Non-limiting examples of suitable inorganic bases include metal hydrides (e.g., NaH), metal hydroxides (e.g., NaOH, KOH), metal alkoxides (e.g., MeONa, t-BuOK and Na-tert-amylate), metal carbonates (e.g., $Na_2CO_3$, $K_2CO_3$, $Cs_2CO_3$), and metal phosphates (e.g., $K_3PO_4$). In a preferred embodiment, the base is MeONa, and the solvent is methanol. In another preferred embodiment, the base is NaOH and the solvent is water. The reaction may be carried out at temperatures between 0° C. and the reflux temperature of the solvent, and generally requires a period of 0.5 to 24 hours for completion, preferably about 0.5 to 5 hours, and more preferably about 1-3 hours, and even more preferably about 1-2 hours. The reaction may be run at ambient pressure. The above-described reaction yields the dihydrothieno[3,2-d]pyrimidine diol of formula I.

The above-described reaction scheme (Scheme 1) is advantageous over known methods of synthesizing the dihydrothieno[3,2-d]pyrimidine diols of formula I, in that it is higher yielding, more efficient, and more cost-effective because it uses urea, which is inexpensive and freely available, instead of costlier reactants such as s-ethylisothiourea hydrobromide. The present process also avoids the unpleasant stench associated with the release of ethanethiol during known methods. Moreover, the present process provides another advantage in that the 3-ureido-dihydrothiophene-2-carboxylic acid alkyl ester of formula IV is a solid intermediate of enhanced stability, which permits its isolation and long-term storage if desired.

The dihydrothiophene carboxylic acid alkyl ester of formula II may be prepared by methods known in the art. For example, a thiol of formula V and an ester of formula VI may be reacted to form a thioether carboxylic acid alkyl ester of formula VII, which can then be cyclized to form the dihydrothiophene carboxylic acid alkyl ester of formula II. A non-limiting exemplary procedure is shown in Scheme 2.

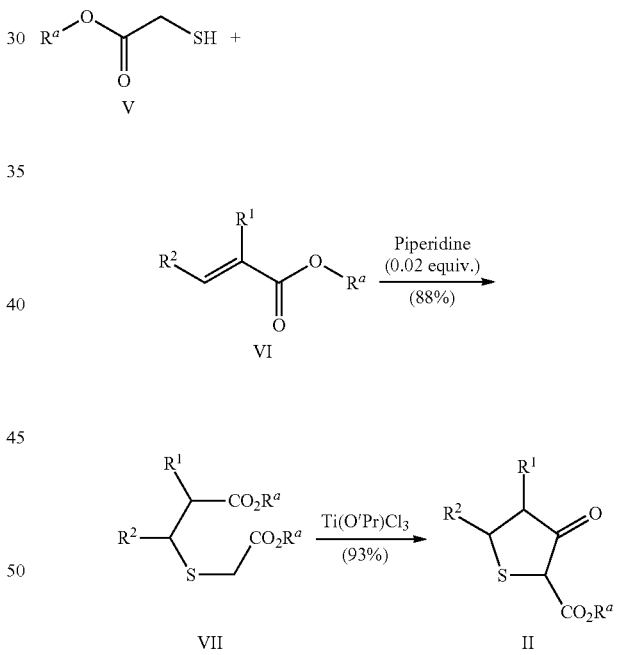

SCHEME 2

As illustrated in Scheme 3, another embodiment of the present invention relates to compounds of formula X that may be prepared starting with an acid-catalyzed condensation between a compound of formula VIII, wherein $R^a$ is alkyl, and urea (III), to yield a compound of formula IX. The compound of formula IX is then cyclized to yield a compound of formula X. The cyclization is preferably performed under basic conditions. The condensation and cyclization reactions may be carried out in separate steps, or may be combined in a "one-pot" procedure. The product, a compound of formula X, may be further modified by methods known in the art to produce additional pyrimidine diol compounds.

SCHEME 3

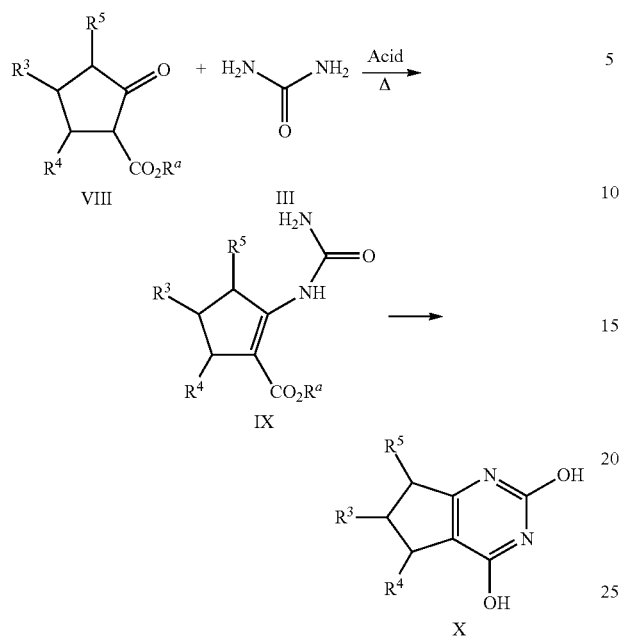

The condensation reaction of the compounds of formulas VIII and III takes place in the presence of an acid catalyst, for example, acetic acid, trifluoroacetic acid, perchloric acid, toluene sulfonic acid, hydrobromic acid, hydrochloric acid, sulfuric acid, or nitric acid. In a preferred embodiment, the acid is a hydrochloric acid. An alcohol or mixture of alcohols may be used as a solvent, for example, methanol, ethanol, isopropanol, n-propanol, butanol, etc., may be used. Methanol is the preferred alcoholic solvent. The reaction may be carried out at temperatures between 0° C. and the reflux temperature of the solvent, and generally requires a period of 0.5 to 24 hours for completion, preferably about 2-6 hours, and more preferably about 4-6 or about 3-5 hours. The reaction may be run at ambient pressure, or at reduced or elevated pressures.

The above-described reaction yields a compound of formula IX, which may be isolated at this time or may be left in the reaction vessel for a "one-pot" procedure. Isolation may be advantageous when removal of impurities is desired before the cyclization process, but is not required.

Whether isolated or not, the compound of formula IX is cyclized, preferably in the presence of a base, in a suitable solvent such as water or an alcohol, for example, methanol, ethanol, isopropanol, n-propanol, butanol, etc. Non-limiting examples of suitable inorganic bases include metal hydrides (e.g., NaH), metal hydroxides (e.g., NaOH, KOH), metal alkoxides (e.g., MeONa, t-BuOK and Na-tert-amylate), metal carbonates (e.g., $Na_2CO_3$, $K_2CO_3$, $Cs_2CO_3$), and metal phosphates (e.g., $K_3PO_4$). In a preferred embodiment, the base is MeONa, and the solvent is methanol. In another preferred embodiment, the base is NaOH and the solvent is water. The reaction may be carried out at temperatures between 0° C. and the reflux temperature of the solvent, and generally requires a period of 0.5 to 24 hours for completion, preferably about 0.5 to 5 hours, and more preferably about 1-3 hours, and even more preferably about 1-2 hours. The reaction may be run at ambient pressure. The above-described reaction yields a substituted pyrimidine-2,4-diol of formula X. The pyrimidine diols of the above-identified embodiments can be used as intermediates to synthesize pharmaceuticals such as PDE4 inhibitors, by methods known in the art.

In one embodiment of the invention, a process for preparing a compound of formula I:

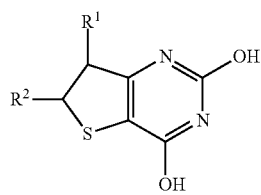

comprises:
(a) reacting a starting compound of the formula II

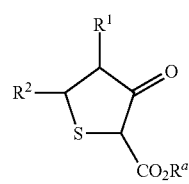

with urea, in the presence of acid, to yield an intermediate of the formula IV

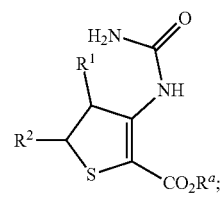

and
(b) cyclizing the intermediate of the formula IV with a base, to yield the final product of the formula I,
wherein $R^1$ and $R^2$ are independently selected from H, alkyl, cycloalkyl, aryl, heteroaryl, heterocycloalkyl, halogen, alkoxy, aryloxy, cycloalkoxy, heteroaryloxy, heterocycloalkoxy, —$NO_2$, —NRR', haloalkyl, haloalkoxy, —SH, —S-alkyl, —$SO_2$-alkyl, —$SO_2NH_2$, —$SO_2$NH-alkyl, and —$SO_2$N(alkyl)$_2$;
wherein R and R' are each independently selected from H or alkyl; and
wherein $R^a$ is selected from the group consisting of H, halogen, alkyl, and aryl.

In a preferred embodiment, $R^1$ and $R^2$ are independently selected from H, alkyl, aryl, alkoxy, halogen, haloalkyl, haloalkoxy and —NRR', wherein R and R' are each independently selected from H or alkyl.

In yet another preferred embodiment, the compound of formula I is 6,7-dihydro-thieno[3,2-d]pyrimidine-2,4-diol, 6-methyl-6,7-dihydro-thieno[3,2-d]pyrimidine-2,4-diol, 6-ethyl-6,7-dihydro-thieno[3,2-d]pyrimidine-2,4-diol, 6-phenyl-6,7-dihydro-thieno[3,2-d]pyrimidine-2,4-diol, 6,6-dimethyl-6,7-dihydro-thieno[3,2-d]pyrimidine-2,4-diol, or 7-methyl-6,7-dihydro-thieno[3,2-d]pyrimidine-2,4-diol.

In another embodiment of the invention, a process for preparing a compound of formula X:

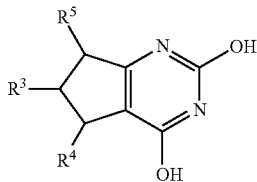

comprises:
(a) reacting a starting compound of the formula VIII

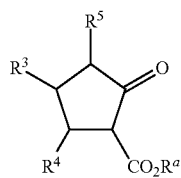

with urea, in the presence of acid, to yield an intermediate of the formula IX

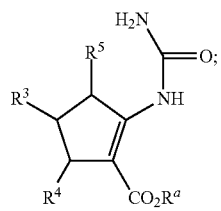

and
(b) cyclizing the intermediate of the formula IX with a base, to yield the final product of the formula X,
wherein $R^3$ and $R^4$ are independently selected from H, alkyl, cycloalkyl, aryl, heteroaryl, heterocycloalkyl, halogen, alkoxy, aryloxy, cycloalkoxy, heteroaryloxy, heterocycloalkoxy, —$NO_2$, —NRR', haloalkyl, haloalkoxy, —SH—, —S-alkyl, —$SO_2$-alkyl, —$SO_2NH_2$, —$SO_2$NH-alkyl, and —$SO_2$N(alkyl)$_2$, with the proviso that $R^3$ and $R^4$ cannot both be H; or $R^3$ and $R^4$ are combined with the carbon atoms to which they are attached to form a ring selected from the group consisting of benzene, pyridine, pyrimidine, pyrazine, cyclohexane, piperidine, piperazine, morpholine, thiomorpholine, a partially or fully hydrated pyrimidine and naphthalene, which optionally may be substituted by a residue selected from among alkyl, cycloalkyl, aryl, heteroaryl, heterocycloalkyl, halogen, alkoxy, aryloxy, cycloalkoxy, heteroaryloxy, heterocycloalkoxy, —$NO_2$, —NRR', haloalkyl, haloalkoxy and hydroxy;

wherein $R^5$ is selected from H, alkyl, cycloalkyl, aryl, heteroaryl, heterocycloalkyl, halogen, alkoxy, aryloxy, cycloalkoxy, heteroaryloxy, heterocycloalkoxy, —$NO_2$, —NRR', haloalkyl, haloalkoxy, —SH, —S-alkyl, —$SO_2$-alkyl, —$SO_2NH_2$, —$SO_2$NH-alkyl, and —$SO_2$N(alkyl)$_2$;

wherein R and R' are each independently selected from H or alkyl; and wherein $R^a$ is selected from the group consisting of H, halogen, alkyl and aryl.

In a preferred embodiment, the compound of formula X is 9H-indeno[2,1-d]pyrimidine-2,4-diol.

Preferably, $R^a$ in the above outlined processes is an alkyl selected from methyl, ethyl, propyl, isopropyl, butyl, isobutyl, sec-butyl or tert-butyl.

Additionally, the acid may be selected from acetic acid, trifluoroacetic acid, perchloric acid, toluene sulfonic acid, hydrobromic acid, hydrochloric acid, sulfuric acid and nitric acid. Preferably, the acid is hydrochloric acid. The base may be selected from the group consisting of metal hydride bases, metal hydroxide bases, metal carbonates, metal alkoxide bases, and metal phosphate bases. Preferably, the base is MeONa or NaOH.

Preferably, in the above outlined processes, the intermediate of the formula IV or formula IX is isolated before cyclizing it in step (b). The isolated intermediate of the formula IV or formula IX is purified by a method known in the art, including column chromatography, HPLC or recrystallization. Alternatively, the intermediate of the formula IV or formula IX is not isolated before cyclizing it in step b).

In another embodiment, the solvent of the step (a) in the above-outlined processes is an alcohol or a mixture of alcohols. The alcohol or mixture of alcohols may be methanol, ethanol, isopropanol, n-propanol, butanol or mixtures thereof. In yet another embodiment, the reaction outlined in step (a) of the above processes is carried out at a temperature between 0° C. and reflux temperature of the solvent, and between 0.5 hour and 24 hours for its completion.

In another embodiment, the solvent of the step (b) in the above-outlined processes is water, an alcohol or a mixture of alcohols. The alcohol or mixture of alcohols may be methanol, ethanol, isopropanol, n-propanol, butanol or mixtures thereof. In yet another embodiment, the cyclization reaction outlined in step (b) of the above processes is carried out at a temperature between 0° C. and reflux temperature of the solvent, and between 0.5 hour and 24 hours for completion.

EXAMPLES

Example 1

Compound III (urea; 2 equiv.) was charged into a flask equipped with a stirrer, $N_2$ line and thermocouple thermometer followed by methanol (3 mL/g of compound IIa) and compound IIa (1 equiv) (see Scheme 4). Conc. HCl (0.2 equiv) was charged at 20-25° C. and the mixture was stirred at reflux for 4 hours. NaOMe (1.2 equiv., 25% solution in MeOH) was charged at 0° C. and the above mixture was stirred at reflux for 1.5 hours and then cooled to 0° C. Conc. HCl was added dropwise until the pH of the solution was 2-3, the mixture was stirred for 5-10 min and the resulting solid was collected by filtration. The cake was washed thoroughly with water, air-dried for 2-3 hours (suction) and then dried further in a vacuum oven at 50° C. for 12-16 hours to afford compound Ia in 80-85% yield from compound IIa.

SCHEME 4

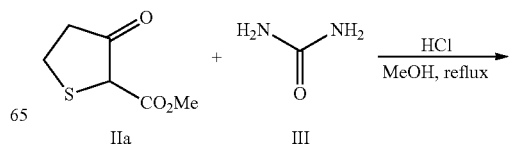

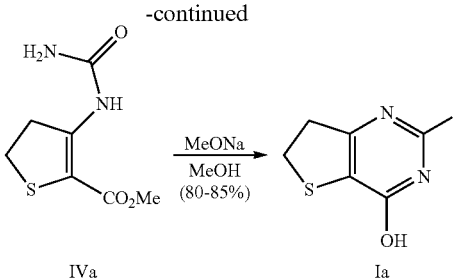

Example 2

3-Ureido-4,5-dihydro-thiophene-2-carboxylic acid methyl ester

Compound III (urea; 2 equiv.) was charged into a vessel equipped with a stirrer, $N_2$ line and thermocouple thermometer followed by methanol (1.5 to 2 mL/g of compound IIa) and compound IIa (1 equiv) (see Scheme 5). Conc. HCl (0.2 equiv) was charged at 20-25° C. and the mixture stirred at reflux for 4-6 hours. The reaction mixture was cooled to 0° C. and the resulting solid was collected by filtration. The cake was washed with water (twice with 1 mL/g of compound IIa) to afford compound IVa as a white solid in 95% yield.

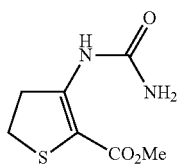
(IVa)

95% yield, $^1$H NMR (500 MHz, $(CD_3)_2SO$) δ 3.10 (dd, 2H, J=8.5, 8.5 Hz), 3.50 (dd, 2H, J=8.5, 8.5 Hz), 3.73 (s, 3H), 6.50-7.20 (bs, 2H), 9.47 (s, 1H); $^{13}$C NMR (125 MHz, $(CD_3)_2SO$) δ 28.7, 37.8, 52.4, 100.0, 151.6, 154.7, 165.7; LCMS (EI) for $C_7H_{11}N_2O_3S$, (M+H)+calcd. 203.0, measd. 203.0.

6,7-Dihydro-thieno[3,2-d]pyrimidine-2,4-diol

Compound IVa was added to a solution of water (3 mL/mL of compound IVa) and NaOH at ambient temperature. The above mixture was stirred at 85° C. for 1.5 hours. After cooling to 0° C., conc. HCl (approximately 1.1 equiv.) was added slowly until the pH of the solution was 0-1. The mixture was cooled to 0° C., stirred for 5-10 min and the resulting solid was collected by filtration. The cake was washed thoroughly with water twice (0.5 mL/g of compound IVa), air-dried for 2-3 hours (suction) and then dried further in a vacuum oven at 50° C. for 12-16 hours to afford compound Ia as a white solid in 95% yield from compound IVa.

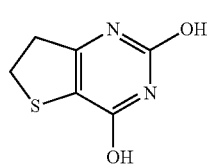
(Ia)

95% yield, $^1$H NMR (500 MHz, $(CD_3)_2SO$) δ 3.11 (dd, 2H, J=8.5, 8.5 Hz), 3.31 (dd, 2H, J=8.5, 8.5 Hz), 11.14 (s, 1H), 11.38 (s, 1H); $^{13}$C NMR (125 MHz, $(CD_3)_2SO$) δ 29.3, 35.4, 108.5, 150.5, 152.4, 160.4; LCMS (EI) for $C_6H_7N_2O_2S$, (M+H)+ calcd. 171.0, measd. 171.0.

SCHEME 5

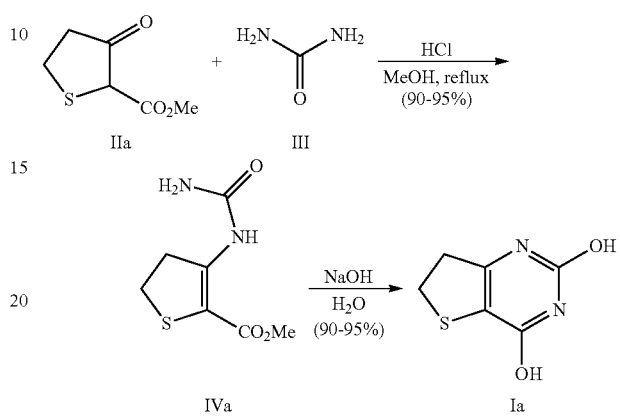

Example 3

5-Methyl-3-ureido-4,5-dihydro-thiophene-2-carboxylic acid methyl ester

Compound III (urea; 2 equiv.) was charged into a vessel equipped with a stirrer, $N_2$ line and thermocouple thermometer followed by methanol (1.5 to 2.0 mL/g of compound IIb) and compound IIb (1 equiv) (see Scheme 6). Conc. HCl (0.2 equiv) was charged at 20-25° C. and the mixture stirred at reflux for 4-6 hours. The reaction mixture was cooled to 0° C. and the resulting solid was collected by filtration. The cake was washed with water (twice with 1 mL/g of compound IIb) to afford compound IVb as a white solid in 93% yield.

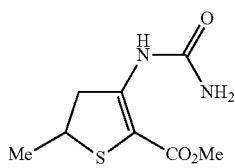
(IVb)

93% yield, $^1$H NMR (400 MHz, $(CD_3)_2SO$) δ 1.32 (d, 3H, J=6.5 Hz), 3.24 (dd, 1H, J=6.5, 18.0 Hz), 3.55-3.73 (m, 2H), 3.72 (s, 3H), 6.40-7.30 (bs, 1H), 9.35-9.65 (bs, 1H); $^{13}$C NMR (100 MHz, $(CD_3)_2SO$) δ 22.8, 40.1, 45.6, 52.3, 99.5, 150.0, 154.7, 165.8; LCMS (EI) for $C_8H_{13}N_2O_3S$, (M+H)+ calcd. 217.1, measd. 217.6.

6-Methyl-6,7-dihydro-thieno[3,2-d]pyrimidine-2,4-diol

Compound IVb was added to a solution of water (3 mL/mL of compound IVb) and NaOH at ambient temperature. The above mixture was stirred at 85° C. for 1.5 hours. After cooling to 0° C., conc. HCl (approximately 1.1 equiv.) was added slowly until the pH of the solution was 0-1. The mixture was cooled to 0° C., stirred for 5-10 min and the resulting solid was collected by filtration. The cake was washed thoroughly with water twice (0.5 mL/g of compound IVb), air-dried for 2-3 hours (suction) and then dried further in a vacuum oven at 50° C. for 12-16 hours to afford compound Ib as a white solid in 90% yield from compound IVb.

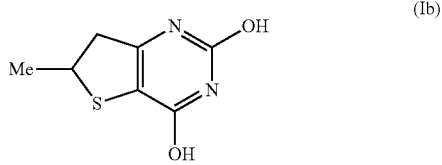 [SMILES: CC1Cc2nc(O)nc(O)c2S1]

90% yield, $^1$H NMR (400 MHz, $(CD_3)_2SO$) δ 1.39 (d, 3H, J=6.5 Hz), 2.75 (dd, 1H, J=6.5, 17.0 Hz), 3.26 (dd, 1H, J=8.5, 17.0 Hz), 3.96 (dddd, 1H, J=6.5, 6.5, 6.5, 13.0 Hz), 11.00-11.20 (bs, 1H), 11.20-11.40 (bs, 1H); $^{13}$C NMR (100 MHz, $(CD_3)_2SO$) δ 23.0, 42.0, 43.0, 108.0, 149.0, 152.4, 160.4; LCMS (EI) for $C_7H_9N_2O_2S$, (M+H)+ calcd. 185.0, measd. 185.1.

SCHEME 6

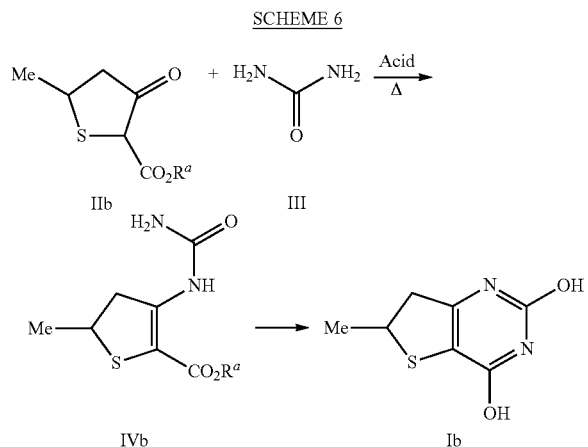

Example 4

5-Ethyl-3-ureido-4,5-dihydro-thiophene-2-carboxylic acid methyl ester

Compound III (urea; 2 equiv.) was charged into a vessel equipped with a stirrer, N$_2$ line and thermocouple thermometer followed by methanol (1.5 to 2 mL/g of compound IIc) and compound IIc (1 equiv) (see Scheme 7). Conc. HCl (0.2 equiv) was charged at 20-25° C. and the mixture stirred at reflux for 4-6 hours. The reaction mixture was cooled to 0° C. and the resulting solid was collected by filtration. The cake was washed with water (twice with 1 mL/g of compound IIc) to afford compound IVc as a white solid in 93% yield.

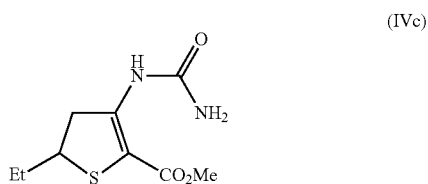

93% yield, $^1$H NMR (500 MHz, $(CD_3)_2SO$) δ 0.93 (t, 3H, J=7.3 Hz), 1.52-1.74 (m, 2H), 3.28 (dd, 1H, J=6.5, 18.0 Hz), 3.53 (dddd, 1H, J=6.0, 6.0, 8.5, 8.5 Hz), 3.61 (dd, 1H, J=8.5, 18.0 Hz), 3.72 (s, 3H), 6.83 (bs, 2H), 9.44 (s, 1H); $^{13}$C NMR (100 MHz, $(CD_3)_2SO$) δ 12.8, 29.7, 43.5, 47.3, 52.3, 99.3, 150.3, 154.7, 165.7; LCMS (EI) for $C_9H_{15}N_2O_3S$, (M+H)+ calcd. 231.1, measd. 231.1.

6-Ethyl-6,7-dihydro-thieno[3,2-d]pyrimidine-2,4-diol

Compound IVc was added to a solution of water (3 mL/mL of compound IVc) and NaOH at ambient temperature. The above mixture was stirred at 85° C. for 1.5 hours. After cooling to 0° C., conc. HCl (approximately 1.1 equiv.) was added slowly until the pH of the solution was 0-1. The mixture was cooled to 0° C., stirred for 5-10 min and the resulting solid was collected by filtration. The cake was washed thoroughly with water twice (0.5 mL/g of compound IVc), air-dried for 2-3 hours (suction) and then dried further in a vacuum oven at 50° C. for 12-16 hours to afford compound Ic as a white solid in 74% yield from compound IVc.

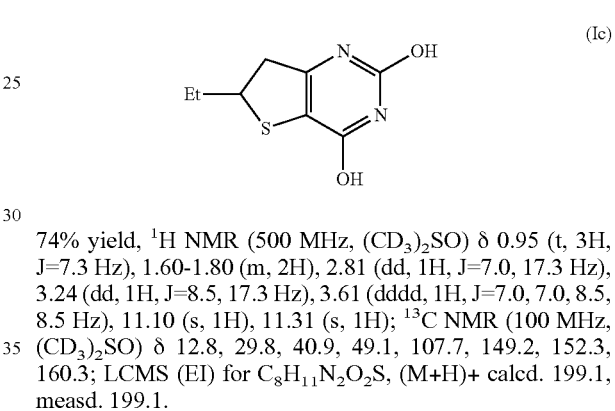

74% yield, $^1$H NMR (500 MHz, $(CD_3)_2SO$) δ 0.95 (t, 3H, J=7.3 Hz), 1.60-1.80 (m, 2H), 2.81 (dd, 1H, J=7.0, 17.3 Hz), 3.24 (dd, 1H, J=8.5, 17.3 Hz), 3.61 (dddd, 1H, J=7.0, 7.0, 8.5, 8.5 Hz), 11.10 (s, 1H), 11.31 (s, 1H); $^{13}$C NMR (100 MHz, $(CD_3)_2SO$) δ 12.8, 29.8, 40.9, 49.1, 107.7, 149.2, 152.3, 160.3; LCMS (EI) for $C_8H_{11}N_2O_2S$, (M+H)+ calcd. 199.1, measd. 199.1.

SCHEME 7

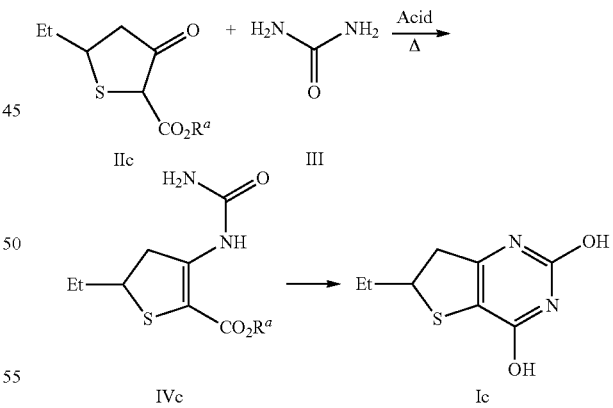

Example 5

5-Phenyl-3-ureido-4,5-dihydro-thiophene-2-carboxylic acid methyl ester

Compound III (urea; 2 equiv.) was charged into a vessel equipped with a stirrer, N$_2$ line and thermocouple thermometer followed by methanol (1.5 to 2 mL/g of compound IId) and compound IId (1 equiv) (see Scheme 8). Conc. HCl (0.2 equiv) was charged at 20-25° C. and the mixture stirred at reflux for 4-6 hours. The reaction mixture was cooled to 0° C. and the resulting solid was collected by filtration. The cake was washed with water (twice with 1 mL/g of compound IId) to afford compound IVd as a white solid in 97% yield.

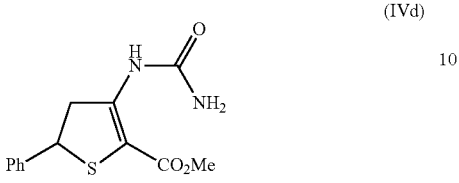

(IVd)

97% yield, $^1$H NMR (500 MHz, $(CD_3)_2SO$) δ 3.70 (dd, 1H, J=8.0, 18.0 Hz), 3.74 (s, 3H), 3.92 (dd, 1H, J=8.0, 18.0 Hz), 4.87 (dd, 1H, J=8.0, 8.0 Hz), 6.60-7.20 (bs, 2H), 7.25-7.50 (m, 5H), 9.51 (s, 1H); $^{13}$C NMR (100 MHz, $(CD_3)_2SO$) δ 45.1, 48.1, 52.4, 99.4, 127.8, 128.3, 129.5, 142.8, 149.5, 154.7, 165.4 (missing 2 signals due to overlap); LCMS (EI) for $C_{13}H_{15}N_2O_3S$, (M+H)+ calcd. 279.1, measd. 279.1.

6-Phenyl-6,7-dihydro-thieno[3,2-d]pyrimidine-2,4-diol

Compound IVd was added to a solution of water (3 mL/mL of compound IVd) and NaOH at ambient temperature. The above mixture was stirred at 85° C. for 1.5 hours. After cooling to 0° C., conc. HCl (approximately 1.1 equiv.) was added slowly until the pH of the solution was 0-1. The mixture was cooled to 0° C., stirred for 5-10 min and the resulting solid was collected by filtration. The cake was washed thoroughly with water twice (0.5 mL/g of compound IVd), air-dried for 2-3 hours (suction) and then dried further in a vacuum oven at 50° C. for 12-16 hours to afford compound Id as a white solid in 89% yield from compound IVd.

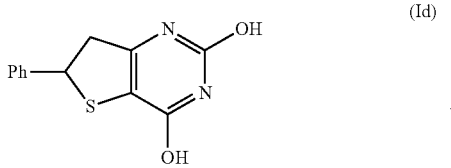

(Id)

89% yield, $^1$H NMR (500 MHz, $(CD_3)_2SO$) 3.29 (dd, 1H, J=8.5, 17.5 Hz), 3.51 (dd, 1H, J=8.5, 17.5 Hz), 5.17 (dd, 1H, J=8.5, 8.5 Hz), 7.30-7.50 (m, 5H), 11.20 (s, 1H), 11.42 (s, 1H); $^{13}$C NMR (125 MHz, $(CD_3)_2SO$) δ 42.7, 49.6, 107.8, 128.0, 128.7, 129.6, 142.0, 148.5, 152.3, 160.1 (missing 2 signals due to overlap); LCMS (EI) for $C_{12}H_{11}N_2O_2S$, (M+H)+ calcd. 247.1, measd. 247.1.

SCHEME 8

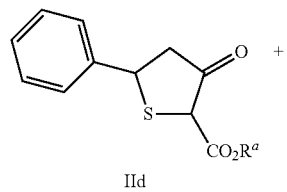

IId

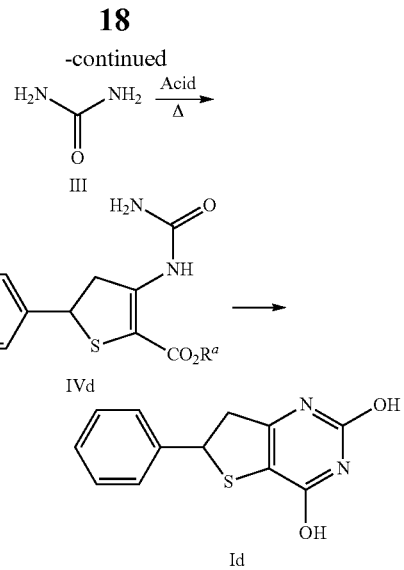

Example 6

5,5-Dimethyl-3-ureido-4,5-dihydro-thiophene-2-carboxylic acid methyl ester

Compound III (urea; 2 equiv.) was charged into a vessel equipped with a stirrer, $N_2$ line and thermocouple thermometer followed by methanol (1.5 to 2 mL/g of compound IIe) and compound IIe (1 equiv) (see Scheme 9). Conc. HCl (0.2 equiv) was charged at 20-25° C. and the mixture stirred at reflux for 4-6 hours. The reaction mixture was cooled to 0° C. and the resulting solid was collected by filtration. The cake was washed with water (twice with 1 mL/g of compound IIe) to afford compound IVe as a white solid in 83% yield.

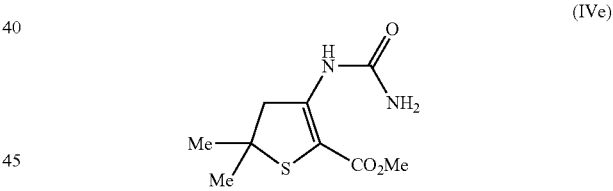

(IVe)

83% yield, $^1$H NMR (400 MHz, $(CD_3)_2SO$) δ 1.46 (s, 6H), 3.38 (s, 2H), 3.71 (s, 3H), 6.60-7.20 (bs, 2H), 9.45 (s, 1H); $^{13}$C NMR (100 MHz, $(CD_3)_2SO$) δ 30.4, 51.6, 52.0, 52.3, 100.2, 149.5, 154.8, 165.8 (1 signal missing due to overlap); LCMS (EI) for $C_9H_{15}N_2O_3S$, (M+H)+ calcd. 231.1, measd. 231.6.

6,6-Dimethyl-6,7-dihydro-thieno[3,2-d]pyrimidine-2,4-diol

Compound IVe was added to a solution of water (3 mL/mL of compound IVe) and NaOH at ambient temperature. The above mixture was stirred at 85° C. for 1.5 hours. After cooling to 0° C., conc. HCl (approximately 1.1 equiv.) was added slowly until the pH of the solution was 0-1. The mixture was cooled to 0° C., stirred for 5-10 min and the resulting solid was collected by filtration. The cake was washed thoroughly with water twice (0.5 mL/g of compound IVe), air-dried for 2-3 hours (suction) and then dried further in a vacuum oven at 50° C. for 12-16 hours to afford compound Ie as a white solid in 90% yield from compound IVe.

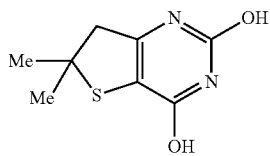

(Ie)

90% yield, ¹H NMR (400 MHz, (CD$_3$)$_2$SO) δ 1.53 (s, 6H), 2.95 (s, 2H), 11.10 (s, 1H), 11.32 (s, 1H); ¹³C NMR (100 MHz, (CD$_3$)$_2$SO) δ 30.7, 49.2, 54.7, 108.4, 148.2, 152.3, 160.5 (1 signal missing due to overlap); LCMS (EI) for C$_8$H$_{11}$N$_2$O$_2$S, (M+H)+ calcd. 199.1, measd. 199.1.

SCHEME 9

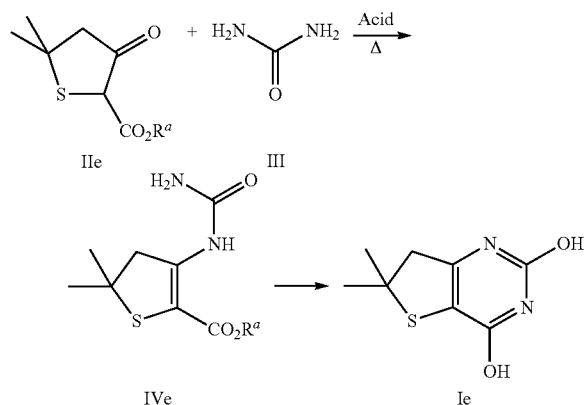

Example 7

4-Methyl-3-ureido-4,5-dihydro-thiophene-2-carboxylic acid methyl ester

Compound III (urea; 2 equiv.) was charged into a vessel equipped with a stirrer, N$_2$ line and thermocouple thermometer followed by methanol (1.5 to 2 mL/g of compound IIf) and compound IIf (1 equiv) (see Scheme 10). Conc. HCl (0.2 equiv) was charged at 20-25° C. and the mixture stirred at reflux for 4-6 hours. The reaction mixture was cooled to 0° C. and the resulting solid was collected by filtration. The cake was washed with water (twice with 1 mL/g of compound IIf) to afford compound IVf as a white solid in 48% yield.

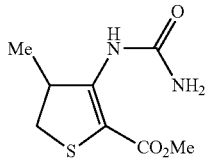

(IVf)

48% yield, ¹H NMR (500 MHz, (CD$_3$)$_2$SO) δ 1.16 (d, 3H, J=7.0 Hz), 2.75 (d, 1H, J=11.0 Hz), 3.20 (dd, 1H, J=7.5, 11.0 Hz), 3.73 (s, 3H), 4.35-4.43 (m, 1H), 6.50-7.20 (m, 2H), 9.40 (s, 1H); ¹³C NMR (125 MHz, (CD$_3$)$_2$SO) δ 16.7, 36.0, 42.0, 52.4, 98.8, 154.3, 155.7, 166.0; LCMS (EI) for C$_8$H$_{13}$N$_2$O$_3$S, (M+H)+ calcd. 217.1, measd. 217.1.

7-Methyl-6,7-dihydro-thieno[3,2-d]pyrimidine-2,4-diol

Compound IVf was added to a solution of water (3 mL/mL of compound IVf) and NaOH at ambient temperature. The above mixture was stirred at 85° C. for 1.5 hours. After cooling to 0° C., conc. HCl (approximately 1.1 equiv.) was added slowly until the pH of the solution was 0-1. The mixture was cooled to 0° C., stirred for 5-10 min and the resulting solid was collected by filtration. The cake was washed thoroughly with water twice (0.5 mL/g of compound IVf), air-dried for 2-3 hours (suction) and then dried further in a vacuum oven at 50° C. for 12-16 hours to afford compound If as a white solid in 89% yield from compound IVf.

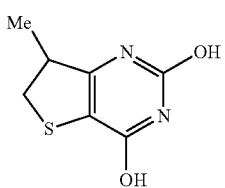

(If)

89% yield, ¹H NMR (500 MHz, (CD$_3$)$_2$SO) δ 1.26 (d, 3H, J=7.0 Hz), 2.92 (dd, 1H, J=5.0, 11.0 Hz), 3.34-3.42 (m, 1H), 3.52 (dd, 1H, J=8.5, 11.0 Hz), 11.17 (s, 1H), 11.34 (s, 1H); ¹³C NMR (125 MHz, (CD$_3$)$_2$SO) δ 17.2, 36.9, 42.3, 107.5, 152.7, 153.7, 160.6; LCMS (EI) for C$_7$H$_9$N$_2$O$_2$S, (M+H)+ calcd. 185.0, measd. 185.2.

SCHEME 10

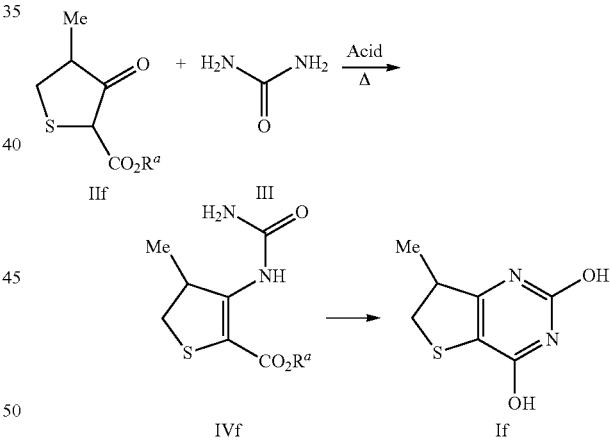

Example 8

2-Ureido-cyclopent-1-enecarboxylic acid methyl ester

Compound III (urea; 2 equiv.) was charged into a vessel equipped with a stirrer, N$_2$ line and thermocouple thermometer followed by methanol (1.5 to 2 mL/g of compound VIIIa) and compound VIIIa (1 equiv) (see Scheme 11). Conc. HCl (0.2 equiv) was charged at 20-25° C. and the mixture stirred at reflux for 4-6 hours. The reaction mixture was cooled to 0° C. and the resulting solid was collected by filtration. The cake was washed with water (twice with 1 mL/g of compound VIIIa) to afford compound IXa as a white solid in 100% yield.

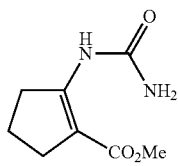

100% yield, $^1$H NMR (400 MHz, (CD$_3$)$_2$SO) δ 1.79 (dt, 2H, J=7.6, 7.6 Hz), 2.43 (t, 2H, J=7.6 Hz), 3.06 (t, 2H, J=7.6 Hz), 3.68 (s, 3H), 6.5-7.0 (bs, 2H), 9.44 (s, 1H); $^{13}$C NMR (100 MHz, (CD$_3$)$_2$SO) δ 21.6, 29.0, 34.9, 51.4, 102.3, 155.1, 157.9, 167.8; LCMS (EI) for C$_8$H$_{13}$N$_2$O$_3$, (M+H)+calcd. 184.1, measd. 185.0.

6,7-Dihydro-5H-cyclopentapyrimidine-2,4-diol

Compound IXa was added to a solution of water (3 mL/mL of compound IXa) and NaOH at ambient temperature. The above mixture was stirred at 85° C. for 1.5 hours. After cooling to 0° C., conc. HCl (approximately 1.1 equiv.) was added slowly until the pH of the solution was 0-1. The mixture was cooled to 0° C., stirred for 5-10 min and the resulting solid was collected by filtration. The cake was washed thoroughly with water twice (0.5 mL/g of compound IXa), air-dried for 2-3 hours (suction) and then dried further in a vacuum oven at 50° C. for 12-16 hours to afford compound Xa as a white solid in 99% yield from compound IXa.

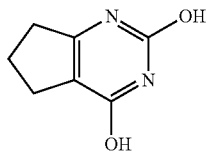

99% yield, $^1$H NMR (500 MHz, (CD$_3$)$_2$SO) δ 1.99 (dt, 2H, J=7.5, 7.5 Hz), 2.48 (t, 2H, J=7.5 Hz), 2.67 (t, 2H, J=7.5 Hz), 10.70 (bs, 1H), 11.05 (bs, 1H); $^{13}$C NMR (100 MHz, (CD$_3$)$_2$SO) δ 21.9, 27.3, 31.9, 110.5, 153.2, 157.0, 162.9; LCMS (EI) for C$_7$H$_9$N$_2$O$_2$, (M+H)+ calcd. 153.1, measd. 153.3.

SCHEME 11

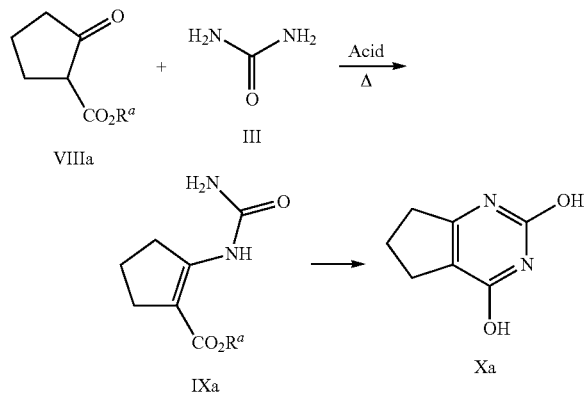

Example 9

2-Ureido-3H-indene-1-carboxylic acid methyl ester

Compound III (urea; 2 equiv.) was charged into a vessel equipped with a stirrer, N$_2$ line and thermocouple thermometer followed by methanol (1.5 to 2 mL/g of compound VIIIb) and compound VIIIb (1 equiv) (see Scheme 11). Conc. HCl (0.2 equiv) was charged at 20-25° C. and the mixture stirred at reflux for 4-6 hours. The reaction mixture was cooled to 0° C. and the resulting solid was collected by filtration. The cake was washed with water (twice with 1 mL/g of compound VIIIb) to afford compound IXb as a white solid in 72% yield.

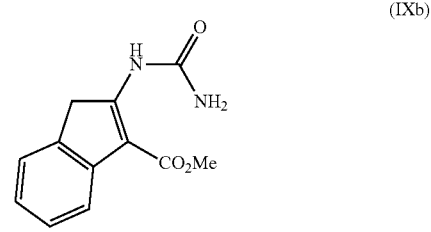 [SMILES: COC(=O)C1=C(NC(N)=O)Cc2ccccc21]

72% yield, $^1$H NMR (500 MHz, (CD$_3$)$_2$SO) δ 3.91 (s, 3H), 4.21 (s, 2H), 6.8-7.4 (bs, 2H), 7.09 (ddd, 1H, J=1.5, 7.5, 7.5 Hz), 7.25 (ddd, 1H, J=1.5, 7.5, 7.5 Hz), 7.40 (d, 1H, J=7.5 Hz), 7.71 (d, 1H, J=7.5 Hz), 10.00 (bs, 1H); $^{13}$C NMR (100 MHz, (CD$_3$)$_2$SO) δ 40.5, 51.9, 105.4, 120.9, 123.8, 124.1, 127.3, 137.1, 140.6, 154.8, 161.5, 167.0; LCMS (EI) for C$_{12}$H$_{13}$N$_2$O$_3$, (M+H)+ calcd. 233.1, measd. 233.2.

9H-Indeno[2,1-d]pyrimidine-2,4-diol

Compound IXb was added to a solution of water (3 mL/mL of compound IXb) and NaOH at ambient temperature. The above mixture was stirred at 85° C. for 1.5 hours. After cooling to 0° C., conc. HCl (approximately 1.1 equiv.) was added slowly until the pH of the solution was 0-1. The mixture was cooled to 0° C., stirred for 5-10 min and the resulting solid was collected by filtration. The cake was washed thoroughly with water twice (0.5 mL/g of compound IXb), air-dried for 2-3 hours (suction) and then dried further in a vacuum oven at 50° C. for 12-16 hours to afford compound Xb as a white solid in 93% yield from compound IXb.

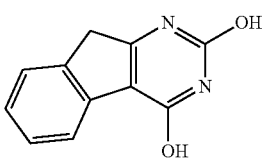

93% yield, $^1$H NMR (500 MHz, (CD$_3$)$_2$SO) δ 3.84 (s, 3H), 7.18 (dd, 1H, J=7.5, 7.5 Hz), 7.31 (dd, 1H, J=7.5, 7.5 Hz), 7.47 (d, 1H, J=7.5 Hz), 7.73 (d, 1H, J=7.5 Hz), 11.13 (bs, 1H), 11.79 (bs, 1H); $^{13}$C NMR (100 MHz, (CD$_3$)$_2$SO) δ 36.6, 111.6, 120.3, 125.0, 125.1, 127.8, 137.6, 139.6, 152.4, 160.0, 161.3; LCMS (EI) for C$_{11}$H$_9$N$_2$O$_2$, (M+H)+ calcd. 201.1, measd. 201.1.

SCHEME 12

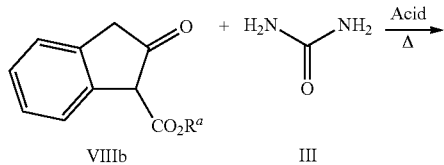

VIIIb    III

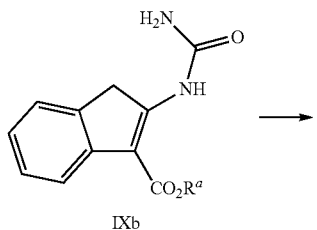

IXb

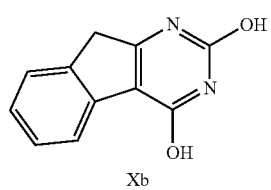

Xb

The above description, drawings and examples are only illustrative of preferred embodiments which achieve the objects, features and advantages of the present invention. It is not intended that the present invention be limited to the illustrative embodiments. Any modification of the present invention which comes within the spirit and scope of the following claims should be considered part of the present invention.

We claim:
1. A process for preparing a compound of formula (I):

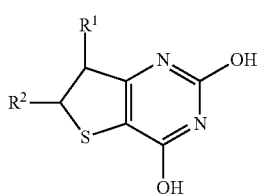

(I)

comprising:
(a) reacting a compound of formula (II)

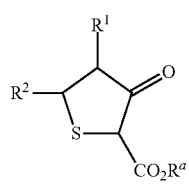

(II)

with urea, in the presence of acid, to yield an intermediate of formula IV

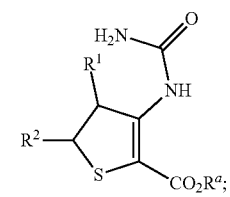

(IV)

and
(b) cyclizing the compound of the formula (IV) with a base, to yield the compound of the formula I,
wherein $R^1$ and $R^2$ are each independently H, alkyl, cycloalkyl, aryl, heteroaryl, heterocycloalkyl, halogen, alkoxy, aryloxy, cycloalkoxy, heteroaryloxy, heterocycloalkoxy, —$NO_2$, —NRR', haloalkyl, haloalkoxy, —SH, —S-alkyl, —$SO_2$-alkyl, —$SO_2NH_2$, —$SO_2$NH-alkyl, or —$SO_2$N(alkyl)$_2$;
wherein R and R' are each independently H or alkyl; and
wherein $R^a$ is H, halogen, alkyl, or aryl.

2. The process of claim 1, wherein $R^1$ and $R^2$ are each independently H, alkyl, aryl, alkoxy, halogen, haloalkyl, haloalkoxy, or —NRR', wherein R and R' are each independently H or alkyl.

3. The process of claim 1, wherein $R^a$ is methyl, ethyl, propyl, isopropyl, butyl, isobutyl, sec-butyl, or tert-butyl.

4. The process of claim 1, wherein the acid is acetic acid, trifluoroacetic acid, perchloric acid, toluene sulfonic acid, hydrobromic acid, hydrochloric acid, sulfuric acid, or nitric acid.

5. The process of claim 1, wherein the acid is hydrochloric acid.

6. The process of claim 1, wherein the base is selected from the group consisting of metal hydride bases, metal hydroxide bases, metal carbonates, metal alkoxide bases, and metal phosphate bases.

7. The process of claim 6, wherein the base is MeONa.

8. The process of claim 6, wherein the base is NaOH.

9. The process of claim 1, wherein the compound of formula (I) is 6,7-dihydro-thieno[3,2-d]pyrimidine-2,4-diol; 6-methyl-6,7-dihydro-thieno[3,2-d]pyrimidine-2,4-diol; 6-ethyl-6,7-dihydro-thieno[3,2-d]pyrimidine-2,4-diol; 6-phenyl-6,7-dihydro-thieno[3,2-d]pyrimidine-2,4-diol; 6,6-dimethyl-6,7-dihydro-thieno[3,2-d]pyrimidine-2,4-diol; or 7-methyl-6,7-dihydro-thieno[3,2-d]pyrimidine-2,4-diol.

10. The process of claim 1, wherein the compound of the formula (IV) is isolated before cyclizing it in step (b).

11. The process of claim 10, wherein the isolated compound of the formula (IV) is also purified.

12. The process of claim 11, wherein the purification method is column chromatography, HPLC, or recrystallization.

13. The process of claim 1, wherein the compound of the formula (IV) is not isolated before cyclizing it in step (b).

14. The process of claim 1, wherein the solvent of the step (a) is an alcohol or a mixture of alcohols.

15. The process of claim 14, wherein the alcohol or mixture of alcohols is methanol, ethanol, isopropanol, n-propanol, butanol, or mixtures thereof.

16. The process of claim 14, wherein the reaction is carried out at a temperature between 0° C. and reflux temperature of the solvent.

17. The process of claim 14, wherein step (a) requires between 0.5 hour and 24 hours for completion.

18. The process of claim 1, wherein the solvent of the step (b) is water, an alcohol, or a mixture of alcohols.

19. The process of claim 18, wherein the alcohol or mixture of alcohols is methanol, ethanol, isopropanol, n-propanol, butanol, or mixtures thereof.

20. The process of claim 18, wherein the cyclization reaction (b) is carried out at a temperature between 0° C. and reflux temperature of the solvent.

21. The process of claim 18, wherein the cyclization reaction (b) requires between 0.5 hour and 24 hours for completion.

* * * * *